United States Patent [19]
Patil et al.

[11] Patent Number: 5,235,101
[45] Date of Patent: Aug. 10, 1993

[54] PREPARATION BY FLOTATION OF OPTICALLY ACTIVE ALIPHATIC CARBOXYLIC ACIDS

[75] Inventors: Deepak R. Patil; Azfar A. Choudhury; Abbas Kadkhodayan, all of Orangeburg, S.C.

[73] Assignee: Ethyl Corporation, Richmond, Va.

[21] Appl. No.: 825,548

[22] Filed: Jan. 24, 1992

[51] Int. Cl.$^5$ .............................................. C07B 57/00
[52] U.S. Cl. ................... 562/401; 548/531; 549/71; 558/414; 560/9; 560/56; 560/61; 560/100; 560/102; 560/105; 560/125; 560/126; 560/128; 560/147; 562/496
[58] Field of Search ............... 562/401, 496; 548/531; 549/71; 560/19, 56, 59, 61, 100, 102, 105, 147, 125, 126, 128; 558/414

[56] References Cited

U.S. PATENT DOCUMENTS

| | | | |
|---|---|---|---|
| 4,694,100 | 9/1987 | Shimizu et al. | 560/105 |
| 4,723,033 | 2/1988 | Erickson | 560/56 |
| 4,752,417 | 6/1988 | Inoue et al. | 562/401 |
| 4,831,147 | 5/1989 | Russell | 562/401 X |
| 4,973,745 | 11/1990 | Blaschke et al. | 562/401 |
| 4,983,765 | 1/1991 | Lukas et al. | 562/401 |
| 5,015,764 | 5/1991 | Manimaran et al. | 562/401 |

*Primary Examiner*—José G. Dees
*Assistant Examiner*—Vera C. Clarke
*Attorney, Agent, or Firm*—Richard J. Hammond

[57] ABSTRACT

An improved process for the separation of enantiomers of a mixture of certain aliphatic carboxylic acids or esters thereof is disclosed. The process involves adding an inert liquid to the reaction solution formed by: (i) forming a salt solution comprising said racemic mixture of a $C_1$ to $C_6$ linear or branched aliphatic carboxylic acid and an organic or inorganic base; (ii) treating said salt solution with less that equimolar equivalents of a chiral organic nitrogenous base; (iii) precipitating from the reaction solution formed in step (ii) the less soluble diastereomeric salt; (iv) addition of a countersolvent to the slurry formed in step (iii); (v) extracting the more soluble diastereomeric salt or the salt of carboxylic acid and the base added in step (i) into the countersolvent. The inert liquid and the countersolvent must be of sufficiently different density. The inert liquid is substantially immiscible with the countersolvent and does not dissolve appreciable quantities of the precipitated less soluble diastereomeric salt.

15 Claims, No Drawings

PREPARATION BY FLOTATION OF OPTICALLY ACTIVE ALIPHATIC CARBOXYLIC ACIDS

FIELD OF INVENTION

This invention relates to an improvement in a process for the preparation of optically active carboxylic acids and the esters thereof. More particularly this invention relates to an improved process for the preparation of aliphatic carboxylic acids and the esters thereof by adding to a mixture of the diastereomeric salts of such materials an inert liquid that has a density less than the density of the mixture and then separating the diastereomeric salts.

BACKGROUND OF THE INVENTION

Resolution of racemic aryl-substituted aliphatic carboxylic acids has been described in the literature. Kaiser et al., *J. Pharm. Sci.*, Vol. 65, No. 2, 269-273 (February 1976) formed the S(−) α-methylbenzylamine salt of S(+)-ibuprofen, removed it from the reaction mixture by filtration, and recrystallized it from isopropanol and then from methanol. After acidifying the 3N aqueous sulfuric acid and extracting with ether, S(+)-ibuprofen was obtained, m.p. 50.14 52., $[\alpha]_D$ +57., with 95% optical purity as determined by GLC analysis. Cox et al., *J. Pharmacol. Exp. Ther.*, Vol. 232, No. 3, 636-643 (March 1985), using the Kaiser et al. method, were able to obtain an S(+)-ibuprofen preparation which was 99% S isomer and 1% R isomer (w/w).

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is less soluble. The (+)-salt can then be acid cleaved to yield pure enantiomer. See, for example, U.S. Pat. No. 4,209,638 issued Jun. 24, 1980, and U.S. Pat. No. 3,637,767 issued Jan. 25, 1972, which relate to resolution of naproxen and related compounds.

U.S. Pat. No. 5,015,764 discloses and claims a process for increasing the amount of the desired enantiomer obtained from a racemic mixture of $C_1$ to $C_6$ linear or branched aliphatic carboxylic acid or ester thereof. The process comprises: (i) forming a salt solution comprising the racemic mixture of the $C_1$ to $C_6$ linear or branched aliphatic carboxylic acid or ester thereof and an organic or inorganic base; (ii) treating said salt solution with a chiral organic nitrogenous base having a base strength no stronger than said organic base, inorganic base or mixtures of an organic base and an inorganic base; (iii) precipitating from the reaction solution produced in the treatment of step (ii) the less soluble diastereomeric salt; and (iv) separating said diastereomeric salt. The disclosure of this patent is incorporated herein by reference.

According to the process of the present invention, an improvement of the above process has been discovered. Reaction steps (i), (ii) and (iii) are carried out as disclosed. At this point in the reaction sequence, a two-phase mixture is produced that is essentially the solid diastereomeric salt and the remaining reaction liquid. The solid is dispersed in near emulsion form throughout the liquid. It is typically separated by filtration leaving the mother liquor filtrate and solid filtered residue. The residue requires numerous recrystallizations before a product of satisfactory purity is obtained. The conventional separation processes are inconvenient and time consuming, disadvantageously producing multiple process streams.

It has now been discovered that an improved crystalline product can be obtained from the mixture of step (iii) by adding an inert liquid having a different density than the density of the reaction mixture. Surprisingly, when the less dense, inert liquid is added and mixed into the reaction mass, when the mixing action is stopped, the solid phase readily separates from both the reaction solvent and the inert liquid. A three-phase mixture typically results, each layer being easily separated from the other by simple mechanical means (decantation and the like). The inert liquid, if less dense than any of the other components of the mixture, usually forms the uppermost layer; if more dense than the other components, usually forms the lowermost layer.

The inert liquid, however, must have appreciable ability to solubilize one of the diastereomeric salts, preferentially more than the other diastereomeric salt. As such, a solubility of 1 gram of salt per cubic centimeter of inert liquid produces an acceptable inert liquid. This characteristic can be readily identified when, after adding a potential inert liquid and mixing, a phase separation occurs. Further, it should be substantially immiscible with the reaction solution. If either of these conditions should occur, then the density of the liquid will be affected and the ability to cause the phase separation will be lost.

Since the process can be carried out in either aqueous or hydrocarbon medium, the inert liquid can be either a hydrocarbon, water, formamide, acetamide, N,N-dialkyl, substituted formamide or acetamide, as long as the above criteria are met. Thus, when reaction steps (i), (ii) and (iii) occur in water, formamide, acetamide, substituted formamide or acetamide as the reaction medium, the inert liquid is an aliphatic or aromatic hydrocarbon optionally substituted with one or more halo (chloro or bromo), nitro, amino, cyano, carboxylic acid or $C_1$ to $C_6$ linear or branched alkyl ester thereof, hydroxy, thio, thioether—the substituent or the sulfur being $C_1$ to $C_6$ linear or branched alkyl, or $C_1$ to $C_6$ linear or branched alkyl, and the reverse is also true.

Preferably, under these reaction conditions, the inert liquid is a $C_5$ to $C_{12}$ linear or branched hydrocarbon optionally substituted with one or more halo groups or it is an aromatic hydrocarbon optionally substituted with one or more $C_1$ to $C_6$ linear or branched alkyl or halo group. Most preferably, the inert liquid is selected from the group consisting essentially of hexane, heptane, octane, benzene, toluene, xylene or mixtures thereof.

When the reaction medium is a hydrocarbon one, water is preferably used as the inert liquid.

The $C_1$ to $C_6$ linear or branched aliphatic carboxylic acids and esters useful in the improved process of the present invention have the formula

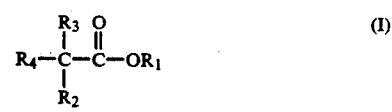

where $R_1$ is hydrogen or $C_1$ to $C_6$ linear or branched alkyl; $R_2$, $R_3$ and $R_4$ are independently the same or different and are hydrogen or $C_1$ to $C_6$ linear or branched alkyl, e.g., methyl or ethyl; aralkyl, e.g., benzyl; $C_3$ to $C_6$ cycloalkyl, e.g., cyclopropyl, cyclobutyl, cyclopentyl, cyclohexyl; alkyl substituted cycloalkyl, e.g., methylcyclohexyl; $C_6$ to $C_{10}$ aryl, e.g., phenyl unsubstituted or substituted with one or more, for example, methyl, dimethyl, butyl, especially isobutyl or phenyl substituted with one or more $C_1$ to $C_4$ alkylthio, $C_1$ to $C_4$ alkoxy, cyano or halo, e.g., fluoro or chloro; $C_1$ to $C_6$ linear or branched aryloxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl, $C_1$ to $C_4$ alkoxy, e.g., ethoxy, halo; or biphenyl unsubstituted or substituted with methyl or halo, especially fluoro.

Preferred compounds of formula I are those of the formula

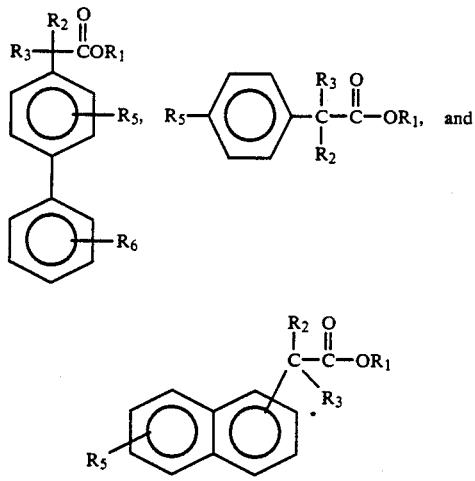

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The improved process is particularly applicable to 2-(4-isobutylphenyl)propionic acid and especially in obtaining a preponderance of the S(+) isomer.

The process is carried out by using a racemic mixture [a mixture of both the (+) and (−) or dextro and levo rotatory forms] or a mixture containing a preponderance of one of the enantiomers of these carboxylic acids. However, it should be understood that in this step, the process itself does not convert one form of the stereoisomers to the other form but only separates such forms. Further, because the separation of isomers gives rise to a soluble product largely containing one enantiomer and an insoluble product largely containing the other enantiomer, a high purity salt is obtained that requires a minimum number of recrystallizations (usually not more than two) to give a product with exceptional high optical purity.

The purified salt obtained from the process of the present invention may be further treated to produce the free aliphatic carboxylic acid thereof by using any conventional means. For example, hydrolysis of the salt an acid and extraction with a suitable solvent produces the purified aliphatic carboxylic acid. Further extraction and recrystallization with a suitable solvent can increase the purity to even greater extent.

The first step in the reaction sequence for the separation of the racemic mixtures used in the present invention is to form a salt solution of the aliphatic carboxylic acid with an organic or inorganic base. Where such organic base is used in this first step, the solvent employed to form the salt solution is preferably an inert liquid. Most preferably, such solvents include the aliphatic hydrocarbon solvents, $C_4$ to $C_{14}$ hydrocarbons, formamide, acetamide, N,N-dialkyl ($C_1$ to $C_6$), substituted formamides or acetamides, e.g., compounds of the formula $R_1C(R_2)HC(O)NH_2$ where $R_1$ and $R_2$ are the same or different and are $C_1$ to $C_6$ linear or branched alkyl, or water. Particularly preferred is hexane, octane or water as such solvent.

The chiral organic nitrogenous base is next added in less than equimolar quantity. It forms a more stable salt with the isomers of the aliphatic carboxylic acid displacing the inorganic or organic base. Further, one of the diastereomeric salts formed from the subsequent displacement of the inorganic or organic base by the chiral organic nitrogenous base is more soluble in the reaction solution (the solution formed when the chiral base is added to the salt solution), the other, of course, precipitates. The solid precipitate is separated from the solution by conventional techniques, i.e., centrifugation, filtration and the like.

The next step in the process is to add the new solvent to extract the unreacted carboxylic acid salt made with the organic or inorganic base. This solvent, referred to as the countersolvent, separates the carboxylic acid chiral base salt from the carboxylic acid organic base salt. If the reaction sequence is conducted in a hydrocarbon solvent, the countersolvent is water, amides, etc. If the reaction sequence is conducted in water, formamide, and the like solvents, the countersolvent is a hydrocarbon solvent.

It should be noted that the process of the present invention achieves the same end result upon change in sequence of addition of the solvents, i.e., the solvent followed by the countersolvent addition, the countersolvent followed by the solvent addition, or the simultaneous addition of solvent and countersolvent perform equally as well.

It should be noted that the process of the present invention is particularly adapted to the economical conversion of mixtures to the diastereomeric S- or (+)-component. (Of course, the R-component may be the least soluble one, in which case the following discussion should be applied in reverse). The method of the present invention essentially provides a solid precipitate enriched in the S-enantiomer suspended in one solvent and a liquid filtrate enriched in the R-enantiomer in another solvent. Liberation of the desired S-enantiomer from the precipitated salt suspended in one solvent is readily accomplished by acidification of the salt with, for example, dilute mineral acid or any other inorganic or organic acid conventionally known to hydrolyze salts of this nature. While this procedure leaves the filtrate as a by-product, it can be further treated with acid or base to convert the R-enriched filtrate to the racemic mixture. This mixture can then be reused in the process of the present invention, using the chiral organic base recovered from the above conversion step. Thus, the process of the present invention lends itself readily to a recycling-type of procedure.

While the above reactions are carried out in a mixture of water and triethylamine, it has been discovered that the aryl-substituted profens (ibuprofen, ketoprofen, etc.) are surprisingly soluble in solvent mixtures of tri $C_1$ to $C_6$ linear or branched aliphatic amines and water (i.e., from 1% amine up to 50% amine). However, when using aryl or aralkyl tertiary amines (such as methylbenzyl amine), such profens display limited or no solubility in mixed water-containing solvent systems. Therefore, these aliphatic amines/water systems can be used to recrystallize these profens.

EXAMPLES

The invention is illustrated by the following Examples.

EXAMPLE 1

To a 3-liter flask equipped with an agitator, thermometer, reflux condenser and an addition funnel were charged 206 grams (1 mole) of racemic ibuprofen, 290 grams of water, and 51 grams (0.5 mole) of triethylamine. The materials in the reactor were heated to 60° C. under vigorous agitation. 60.5 grams (0.5 mole) of (S)-methylbenzyl amine were fed to the reactor over two hours. Crystals of ibuprofen (S)-methylbenzyl amine salt precipitated during the course of the reaction. The reactor contents were further agitated for two hours. At the end of the ride, 350 grams of hexane were added to the reactor and agitated for 15 minutes. The reaction mass was then settled and the ibuprofen (S)-methylbenzyl amine salt was suspended in the less dense hexane phase, while the unreacted ibuprofen stayed in solution in the water phase. The aqueous phase was then drained off and the salt in the hexane phase was washed further with water to remove unreacted ibuprofen. The salt was then filtered from hexane and dried to recover 155 grams of ibuprofen (S)-methylbenzyl amine salt [95% yield based on (S)-methylbenzyl amine charged]. The ibuprofen recovered from this salt was enriched in S-enantiomer (76%-S).

EXAMPLE 2

Using the method described in Example 1, the salt of ibuprofen (S)-methylbenzyl amine (163 grams, 76% S-enantiomer) was prepared in 350 grams of hexane instead of water. The unreacted ibuprofen remained in solution in triethylamine/hexane mixture, while ibuprofen (S)-methylbenzyl amine salt was suspended in hexane. Then 290 grams of water were added to the reactor and the whole agitated for another 15 minutes. The reaction mass was settled and the ibuprofen (S)-methylbenzyl amine salt still remained insoluble and suspended in the hexane phase while the unreacted ibuprofen was extracted in the aqueous phase. The aqueous phase was then drained and the organic phase was water washed. The salt was filtered, dried and analyzed [155 grams—95% yield based on (S)-methylbenzyl amine]. The ibuprofen recovered from this salt contained 75% (S)-enantiomer.

EXAMPLE 3

Using the method described in Example 1, the salt of ibuprofen (S)-methylbenzyl amine was prepared in hexane and water. The unreacted ibuprofen remained in solution in triethylamine/water mixture while ibuprofen (S)-methylbenzyl amine salt was suspended in hexane. The aqueous phase was then drained and the organic phase was water washed. The salt was filtered, dried and analyzed [156 grams—95% yield based on (S)-methylbenzyl amine]. The ibuprofen recovered from this salt contained 76% (S)-enantiomer. The ibuprofen recovered from the aqueous phase contained 73% (R)-enantiomer.

EXAMPLE 4

Using the method described in Example 1, the salt of ibuprofen (S)-methylbenzyl amine (163 grams, 76% S-enantiomer) was prepared in 290 grams of dimethyl formamide instead of water. Once again the ibuprofen (S)-methylbenzyl amine salt was suspended in insoluble and less dense hexane phase. The unreacted ibuprofen was solubilized in triethylamine/dimethyl formamide layer and separated via decantation. The salt in hexane phase was water washed to remove remaining free (S)-methylbenzyl amine and ibuprofen. The salt was then filtered, dried and analyzed. 144 grams ibuprofen (S)-methylbenzyl amine salt were recovered which means 88% yield based on (S)-methylbenzyl amine.

EXAMPLE 5

Repeating the procedure from Example 4, but substituting formamide for dimethyl formamide, afforded 145 grams of ibuprofen (S)-methylbenzyl amine salt [89% yield on (S)-methylbenzyl amine].

We claim:

1. In a process for separating the enantiomers of a racemic mixture of a $C_1$ to $C_6$ linear or branched aliphatic carboxylic acid or ester thereof having the formula:

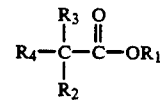

$$R_4 - \underset{\underset{R_2}{|}}{\overset{\overset{R_3}{|}}{C}} - \overset{\overset{O}{\|}}{C} - OR_1 \qquad I$$

where $R_1$ is hydrogen or $C_1$ to $C_6$ linear or branched alkyl; $R_2$, $R_3$ and $R_4$ are different and are hydrogen or $C_1$ to $C_6$ linear or branched alkyl; cycloalkyl; alkyl substituted cycloalkyl; $C_6$ to $C_{14}$ aryl; $C_1$ to $C_6$ linear or branched alkoxy; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; $C_4$ to $C_5$ heteroaryl; the process comprising: (i) forming a salt solution of said racemic mixture and an organic or inorganic base and a suitable solvent; (ii) treating said salt solution with a chiral organic nitrogenous base; (iii) precipitating from the reaction solution formed in step (ii) the less soluble diasteromeric salt; (iv) adding a countersolvent to the slurry formed in step (iii); and (v) extracting the more soluble diastereomeric salt or the salt of carboxylic acid and the base added in step (i) into the countersolvent; the improvement comprising separating the precipitated less soluble diasteromeric salt by adding an inert liquid that: (a) has a density different than the density of the countersolvent; (b) is substantially immiscible with the countersolvent; and (c) does not dissolve appreciable quantities of the precipitated less soluble diastereomeric salt.

2. The process according to claim 1 wherein the solvent is water, formamide or dimethyl formamide, acetamide and the inert liquid is an aliphatic or aromatic hydrocarbon unsubstituted or substituted with one or more alkyl, halo, nitro, cyano, ether, thio, or thioether group.

3. The process according to claim 1 wherein the solvent is an aliphatic or aromatic hydrocarbon unsubstituted or substituted with one or more alkyl, halo, nitro, cyano, thio, or thioether group; and the countersolvent is water, formamide, acetamide, N,N-dialkyl substituted formamides or acetamides, carboxylic acid or ester thereof $C_1$ to $C_6$ linear or branched aliphatic alcohol.

4. The process according to claim 2 wherein the inert liquid is a $C_5$ to $C_{12}$ linear or branched aliphatic hydrocarbon unsubstituted or substituted with one or more halo groups or an aromatic hydrocarbon substituted with alkyl or halo.

5. The process according to claim 1 wherein the inert liquid is water, formamide, acetamide N, N-dialkyl, substituted formamides or acetamides, carboxylic acids or esters thereof, or hydroxy compounds.

6. The process according to claim 1 wherein the inert liquid is selected from the group consisting of hexane, heptane, octane, benzene, toluene, xylene and mixtures thereof.

7. The process according the claim 6 wherein the solvent for the reaction solution is an aliphatic or aromatic hydrocarbon solvent and the inert liquid is water.

8. In a process for separating the diastereomers from a mixture of 2-(4-isobutylphenyl)propionic acid which process comprises: (i) forming a salt solution comprising said mixture and an organic base and a suitable solvent; (ii) treating said salt solution at a temperature of about 25° C. to about 125° C. with a chiral organic base $C_1$ to $C_6$ linear or branched aliphatic amine further substituted with $C_6$ to $C_{10}$ aryl group that is unsubstituted or substituted with $C_1$ to $C_6$ alkyl, $C_1$ to $C_6$ alkoxy or halo, or $C_1$ to $C_6$ linear or branched alkoxy; (iii) precipitating from the reaction solution formed in step (ii) the less soluble diastereomeric salt; (iv) addition of a countersolvent to the slurry formed in step (iii); and (v) extracting the more soluble diastereomeric salt or the salt of carboxylic acid and the base added in step (i) into the countersolvent; the improvement comprising separating the precipitated less soluble diastereomeric salt by adding an inert liquid that: (a) has a density different than the density of the countersolvent; (b) is substantially immiscible with the countersolvent; and (c) doe not dissolve appreciable quantities of the precipitated less soluble diastereomeric salt.

9. The process according to claim 8 wherein the reaction solution is an aqueous reaction solution and the inert liquid is an aliphatic or aromatic hydrocarbon unsubstituted or substituted with one or more alkyl, halo, nitro, cyano, carboxylic acid or ester thereof, hydroxy, thio, thioether group.

10. The process according to claim 9 wherein the inert liquid is a $C_5$ to $C_{12}$ linear or branched aliphatic hydrocarbon unsubstituted or substituted with one or more halo groups or an aromatic hydrocarbon substituted with alkyl or halo.

11. The process according to claim 8 wherein the inert liquid is selected from the group consisting of hexane, heptane, octane, benzene, toluene, xylene and mixtures thereof.

12. The process according to claim 8 wherein the solvent for the reaction solution is an aliphatic or aromatic hydrocarbon solvent and the inert liquid is water.

13. The process of claim 8 wherein said separated salt is hydrolyzed and the free optically active 2-(4-isobutylphenyl)propionic acid and the chiral amine are recovered.

14. The process of claim 13 wherein said optically active 2-(4-isobutylphenyl)propionic acid has S(+) configuration.

15. The process of claim 8 wherein a residual solution is obtained after separation of the precipitated salt containing the more soluble salt of R-enantiomer and said residual solution is treated to racemize said salt of R-enantiomer into the salt of racemic (R,S) mixture for recycling.

* * * * *